US008265772B2

(12) United States Patent
Fallik

(10) Patent No.: US 8,265,772 B2
(45) Date of Patent: Sep. 11, 2012

(54) 3D MICROWAVE SYSTEM AND METHODS

(76) Inventor: Joel Fallik, Catskill, NY (US)

( * ) Notice: Subject to any disclaimer, the term of this patent is extended or adjusted under 35 U.S.C. 154(b) by 1032 days.

(21) Appl. No.: 12/191,457

(22) Filed: Aug. 14, 2008

(65) Prior Publication Data

US 2009/0118803 A1 May 7, 2009

Related U.S. Application Data

(63) Continuation-in-part of application No. 11/174,017, filed on Jul. 1, 2005, now abandoned.

(60) Provisional application No. 61/070,805, filed on Mar. 26, 2008, provisional application No. 60/584,651, filed on Jul. 1, 2004.

(51) Int. Cl.
*A61F 2/00* (2006.01)
*A61F 7/00* (2006.01)
*A61N 1/00* (2006.01)

(52) U.S. Cl. ......... 607/101; 607/100; 607/112; 607/156

(58) Field of Classification Search .................. 607/1–3, 607/61–63, 101, 102, 104, 112, 148, 154–156
See application file for complete search history.

(56) References Cited

U.S. PATENT DOCUMENTS

| | | | |
|---|---|---|---|
| 4,046,139 A | 9/1977 | Horn | |
| 4,230,129 A * | 10/1980 | LeVeen | 607/154 |
| 4,248,245 A | 2/1981 | Kempin | |
| 4,453,552 A * | 6/1984 | Ensign | 600/549 |
| 5,186,181 A | 2/1993 | Franconi | |
| 5,810,888 A | 9/1998 | Fenn | |
| 5,922,013 A * | 7/1999 | Fallik | 607/101 |
| 6,371,112 B1 | 4/2002 | Bibi | |
| 6,416,532 B1 * | 7/2002 | Fallik | 607/109 |
| 2004/0009459 A1 | 1/2004 | Anderson | |
| 2006/0025700 A1 | 2/2006 | Fallik | |
| 2006/0190063 A1 * | 8/2006 | Kanzius | 607/101 |

OTHER PUBLICATIONS

Jeff Garff, "A History of Rife's Instruments and Frequencies," AAA Production Inc., Jun. 4, 2008.
International Search Report and Written Opinion from PCT/US09/53809 issued Nov. 13, 2009.

* cited by examiner

*Primary Examiner* — Nicholas Lucchesi
*Assistant Examiner* — Leah Stohr
(74) *Attorney, Agent, or Firm* — Ronald Abramson; Hughes Hubbard & Reed LLP

(57) ABSTRACT

A therapeutic microwave system comprises a support unit having two or more separable segments; a microwave power assembly positioned between two separated segments of the support unit and including two or more microwave power supply devices; position adjustment componentry; and a central processing unit. The system may further include a temperature sensor for monitoring a treated subject's exhaled air temperature in real time and adjusting microwave irradiation accordingly, and a cooling device for controlling the patient's brain temperature during treatment.

6 Claims, 7 Drawing Sheets

3D MICROWAVE SYSTEM AND METHODS

RELATED APPLICATIONS

This application is a continuation-in-part application of U.S. patent Application Ser. No. 11/174,017 filed on Jul. 1, 2005, published as U.S. Pat. Pub. No. US 2006/0025700, for "Method and apparatus for measuring lung temperature in real time", now abandoned, and claims the benefit of the filing dates of U.S. Provisional patent Application No. 61/070,805 filed on Mar. 26, 2008 and 60/584,651 filed Jul. 1, 2004. Said applications are hereby incorporated by reference in their entirety.

STATEMENT REGARDING FEDERALLY FUNDED RESEARCH

Not applicable.

FIELD OF THE INVENTION

The invention provides a microwave system and methods of treatment that are effective in the treatment of a variety of medical disorders.

BACKGROUND OF THE INVENTION

In various situations it may become desirable to warm or heat a body portion of a subject on a relatively rapid, but controlled basis, in order to achieve a predetermined level of warming. While various methods and approaches have been available for such purposes, they have tended to be slow, ineffective or not readily controllable as to the degree of warming or heating achieved. It has also been difficult to control the positional application and effects to selected areas, relative to other body portions. Certain other mediums, such as x-rays, are difficult to contain and potentially injurious to operators and patients. Also, many potential approaches and mediums capable of providing body heating are not amenable to heating of a subject's entire or substantially entire body on a readily controllable basis.

The microwave body heating system disclosed in U.S. Pat. No. 5,922,013 uses two or more focused waves of microwave energy. A fan wave or transversely scanned wave is directed to a narrow transverse section of a subject's body. The transversely scanned or fan wave is moved longitudinally down the body in a controlled sequential incremental manner. Scanning times, patterns and radiated power levels are controlled in predetermined or monitored formats to achieve desired levels of heating of an entire body or localized area. Microwave frequency energy is provided by two or more magnetron type devices in a variably positionable microwave power assembly, which is longitudinally scanned under control of a robotic motor. The complete disclosure of U.S. Pat. No. 5,922,013 is hereby incorporated by reference.

Modem microwave systems for therapeutic use are based on a magnetron element for generation of microwave energy. A magnetron is a high-powered vacuum tube that generates coherent microwaves. A magnetron works by providing a plurality of resonating cavities arrayed around a central cavity that act to induce a resonant field within the central cavity, which can be directed into a waveguide for delivery and use. By default, the waveform that emits from a magnetron is approximately sinusoidal. Investigators have experimented with a variety of frequencies to kill microorganisms. Work by Dr. Royal Raymond Rife and others showed that audio frequencies with a square wave could be therapeutically effective.

Notwithstanding the therapeutic advancements described in U.S. Pat. No. 5,922,013, the need continues to exist for systems and methods of treatment that optimally apply microwave therapies in a non-injurious manner. This need proves particularly acute in the treatment of illnesses such as tuberculosis and lung cancer, where treated lung cells are temperature-sensitive and can prove to be particularly susceptible to microwave heating.

SUMMARY OF THE INVENTION

In one embodiment, the invention provides a system that heats body portions using controlled microwave energy. The system comprises a support unit that may be comprised of two or more separable segments and that is adapted to support a subject or subject body portion. A microwave power assembly is adapted for the receipt of the subject or subject body portion and may be positioned between two separated segments of the support unit. The microwave power assembly is adapted to move translationally in an axial direction relative to the sectioned support unit (e.g., by affixation to upright, track-mounted supports) and comprises two or more microwave power supply devices that are moveably mounted to a support frame (e.g., an annular support frame) and that are adapted to move radially, circumferentially, and/or translationally, either independently or in tandem with one another. Each of the microwave power supply devices is capable of emitting a focused directional wave of microwave frequency energy at a controllable power level.

Position adjustment elements such as a robotic arm are provided to electromechanically position the microwave power assembly and the two or more microwave power supply devices. As described further hereinafter, in certain embodiments, the two or more microwave power supply devices comprise antennas that can move radially, circumferentially, or translationally, either independently or in tandem (jointly) with one another.

A central processor unit in electronic communication with the position adjustment elements and the two or more microwave power supply devices controls the positioning of the microwave power assembly and the two or more microwave power supply devices, and also controls at least one of the power levels, the wave focus, the wavelength, phase, wave direction, and waveform of each of the waves of microwave frequency energy emitted by the two or more microwave power supply devices.

In another preferred embodiment, the two or more microwave power supply devices generate square wave microwaves.

In another preferred embodiment, the aforementioned systems of the invention comprise means for detecting the temperature of air exhaled by the subject and adjusting irradiation based on exhaled air temperature. The means for detecting the temperature of air exhaled by the subject can include means for anesthetizing the subject.

In still another preferred embodiment, the invention provides a noninvasive mechanism for measuring the temperature of the lungs in real time. In general, this embodiment involves measuring the temperature of outflowing, exhaled air and deriving internal lung temperature as a function of this and other measurements.

In other embodiments, the invention provides methods of treatment that use the aforementioned system.

By facilitating optimum subject orientation and placement during treatment, improving microwave targeting, and enabling real-time monitoring of a subject's lung temperature during treatment, the invention improves on known microwave therapies and proves particularly useful in the treatment of disorders such as tuberculosis and lung cancer. Specifically, systems and methods of the invention achieve deeper microwave penetration through the skin of a treated subject. Skin burning is eliminated by moving the microwave power supply devices relative to the patient's skin surface, to avoid dwelling on any spot for an excessive period. Further, robotic systems of the invention enable continuous targeting of one internal portion of the body while changing the skin area that is subject to irradiation.

These and other aspects of the invention are explained further in the following detailed description of the invention.

DETAILED DESCRIPTION OF THE PREFERRED EMBODIMENTS

The following is a description of alternative preferred embodiments of the invention. These embodiments are illustrative only, and the invention, as defined by the claims, is by no means limited to particular examples shown. For example, certain preferred embodiments are described in relation to an implementation with specific fasteners, sensors and tubing, but it should be appreciated that the disclosure that follows was intended to enable those skilled in the art readily to apply the teachings set forth to other commonly available hardware and electronics. The specific features of any particular embodiment should not be understood as limiting the scope of what may be claimed.

Figure 1:
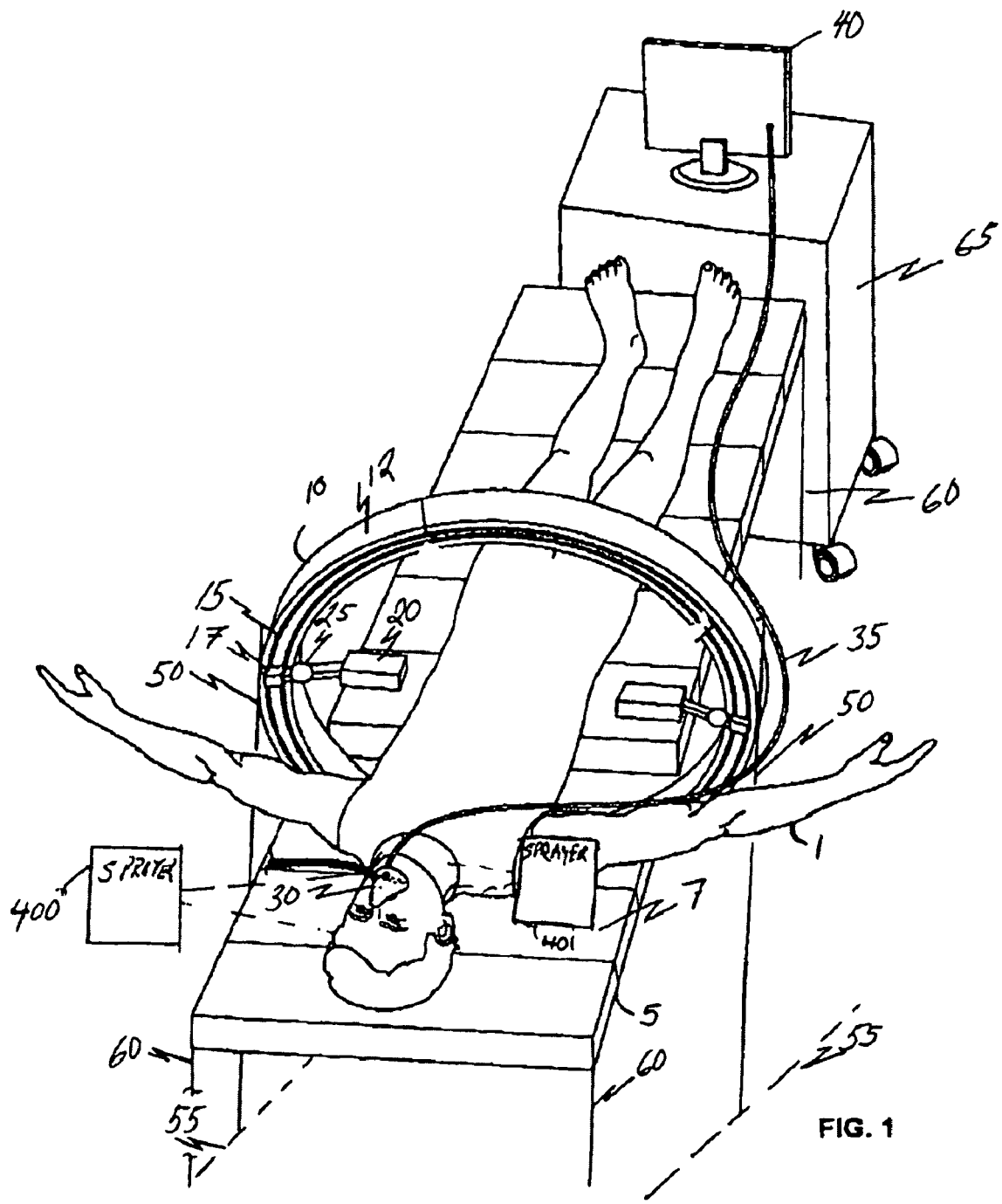
FIG. 1 is a schematic perspective view of one embodiment of a system of the invention and the positioning of a subject during one stage of treatment using such a system.

As illustrated in FIG. 1, a subject 1 is disposed face-up on a support unit 5 which is comprised of a plurality of separable segments 7 and which is supported by legs 60. The segments 7 are separated from one another and selectively removable and replaceable so as to provide a repositionable opening for receiving the bottom portion of translationally moveable microwave power assembly 10 at the desired axial (head-to-foot) position. A microwave power assembly 10 is disposed between two separated segments of support unit 5. As noted above, Microwave power assembly 10 is axially translationally movable relative to support unit 5, and repositionable with respect thereto by removing and replacing the appropriate segments 7 and translationally moving microwave power assembly 10 to the desired axial position. Microwave power assembly 10 is adapted for the receipt of subject 1. Microwave power assembly 10 comprises an annular support frame or housing 12 and microwave power supply devices or sources 20 (e.g., magnetrons with antennas, not separately labeled), that are affixed to support rings 15 via respective movable couplings 17 and robotic arms 25, and adapted to move, alternately independently and in tandem (jointly) with one another, radially and/or circumferentially relative to support frame or housing 12, and translationally therewith. Thus, subject to the control of a central processor unit 40 (described further hereinafter), support rings 15 allow microwave power supply devices 20 to move independently of each other in a radial direction relative to support housing 12, and as a unit with no relative movement between each other.

Each of the two or more microwave power supply devices 20 is capable of emitting a focused directional wave of microwave frequency energy at a controllable power level. Microwave power supply devices 20 can be repositioned by robotic arms 25, e.g., they can be extended and retracted to change their radial positions from center (distance from the treatment point). The two or more microwave power supply devices 20 transmit cancelling/reinforcing wave patterns and allow microwave energy to be focused on a surface, line, point or volume.

Subject 1 is positioned so that his head is beyond the range of axial motion of the microwave power assembly 10 in order to avoid harmful head irradiation. The two or more microwave power supply devices 20 are mounted via couplings 17 on the head-facing side of the support rings 15. That is so that when microwave power assembly 10 is positioned in its most head-ward position, support rings 15 will still be positioned well below the heads allowing clear access for a breathing port element (e.g., breathing mask) 30. Radial movement via support rings 15, and/or movement toward and away from the patient via robotic arms 25, is applied during treatment to keep the point of application of microwave energy in motion relative to the patient's skin surface, to eliminate skin burning.

Microwave power assembly 10 is adapted to move translationally in an axial direction relative to support unit 5 by affixation to supports 50 (FIGS. 1 and 4) that engage and are adapted for translational movement along tracks 55. Before microwave power assembly 10 moves translationally in an axial direction relative to support unit 5, subject 1 must be shifted and appropriate segments 7 must be removed, repositioned and replaced.

A central processor unit 40 is supported on a table 65, is in electronic communication with microwave power supply devices or sources 20 and robotic arms 25 and couplings 17, is adapted to control the positioning of microwave power assembly 10 and the two or more microwave power supply devices 20 by repositioning of robotic arms 25, and is arranged to control at least one of the power level, the wave focus, the wavelength, frequency, phase, wave direction, and waveform of each of said waves of microwave frequency energy emitted by microwave power supply devices 20. Central processor unit 40 includes a memory unit, a keyboard unit, and a display unit, together with such additional computer components and programming as may suitably be provided by skilled persons.

As explained more fully below in the descriptions of FIGS. 6 and 7, the breathing port element (e.g., breathing mask) 30 can include means for detecting the temperature of air exhaled by subject 1. The means for detecting the temperature of air exhaled by subject 1 are in electronic communication through line 35 with central processor unit 40 to correlate and control microwave emission based on the temperature of air exhaled by subject 1.

Sprayers 400 and 401 in FIG. 1 each generate a fine mist of coolant to effect a rapid and controlled cooling of the brain of a patient, as explained further hereinafter.

Figure 2:
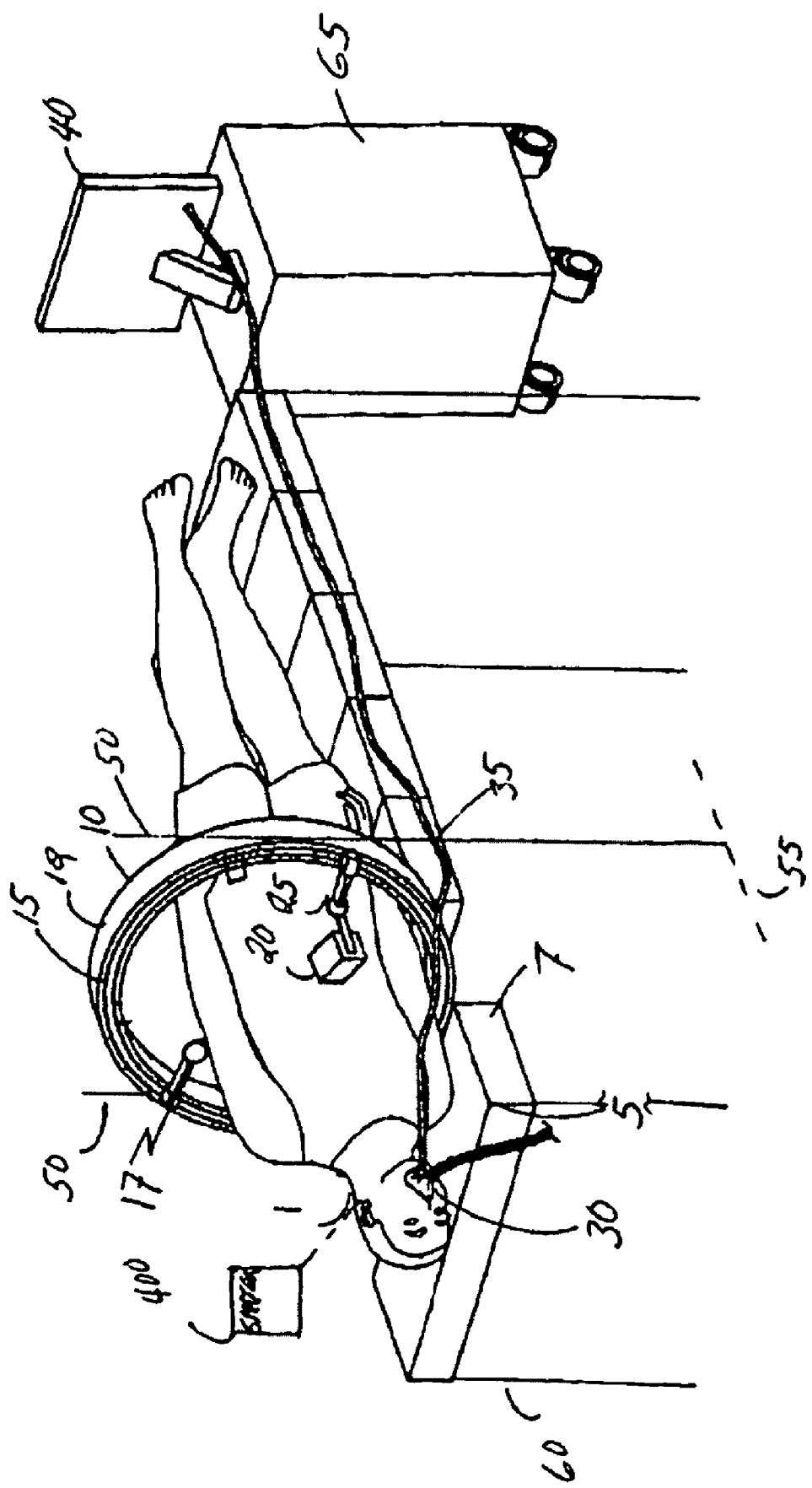
FIG. 2 is a schematic perspective view of one embodiment of a system of the invention and the lateral positioning of a subject during one stage of treatment using such a system.

FIG. 2 illustrates the same system embodiment as that shown in FIG. 1, except that subject 1 in FIG. 2 is positioned on his side. Alternatively, subject 1 can remain on his back, and sources 20 can be rotated to the same effect.

Figure 3:
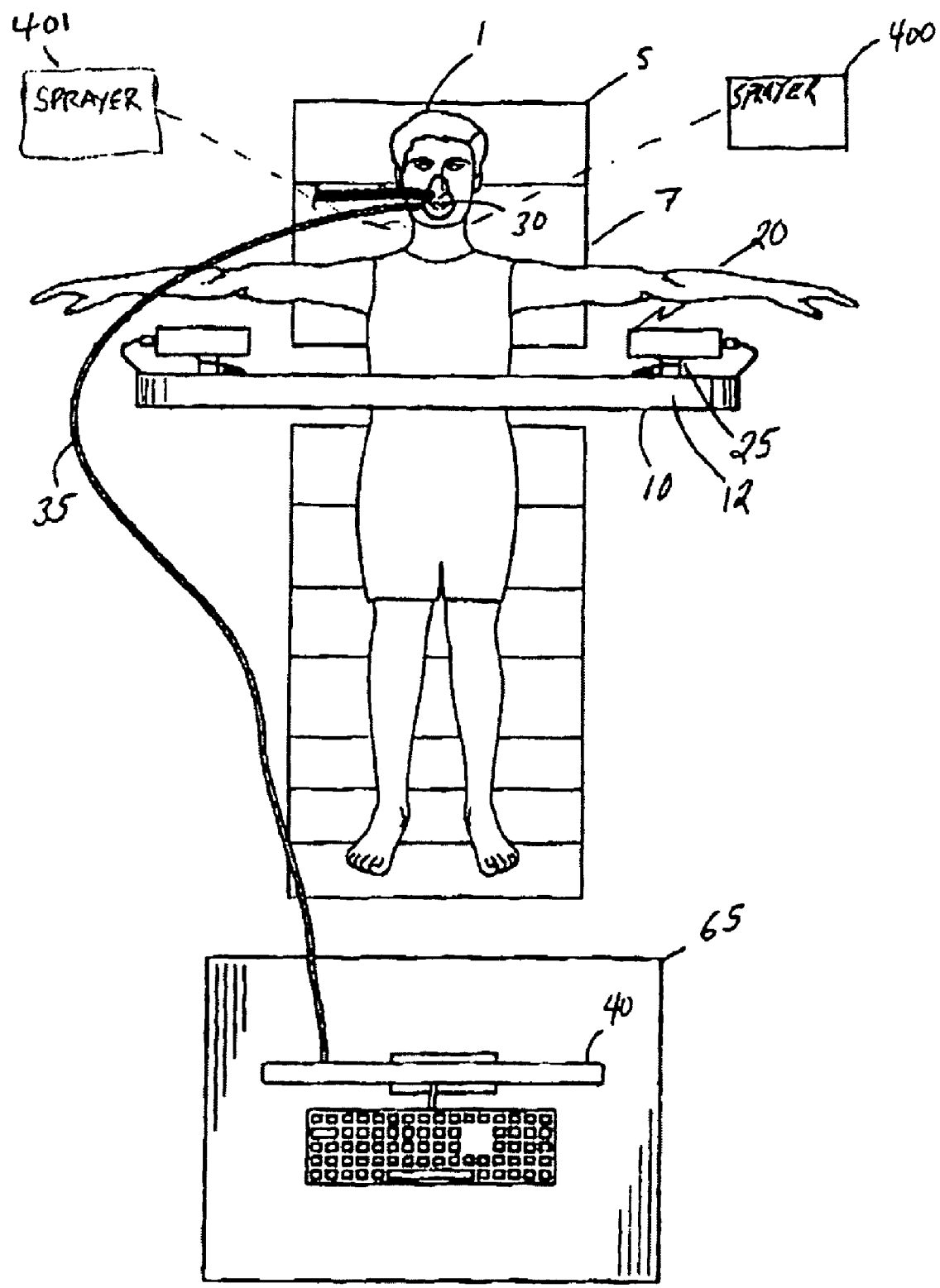
FIG. 3 is a schematic plan view of one embodiment of a system of the invention and the positioning of a subject during one stage of treatment using such a system.

FIG. 3 is a plan view of the system depicted in FIG. 1.

Figure 4:
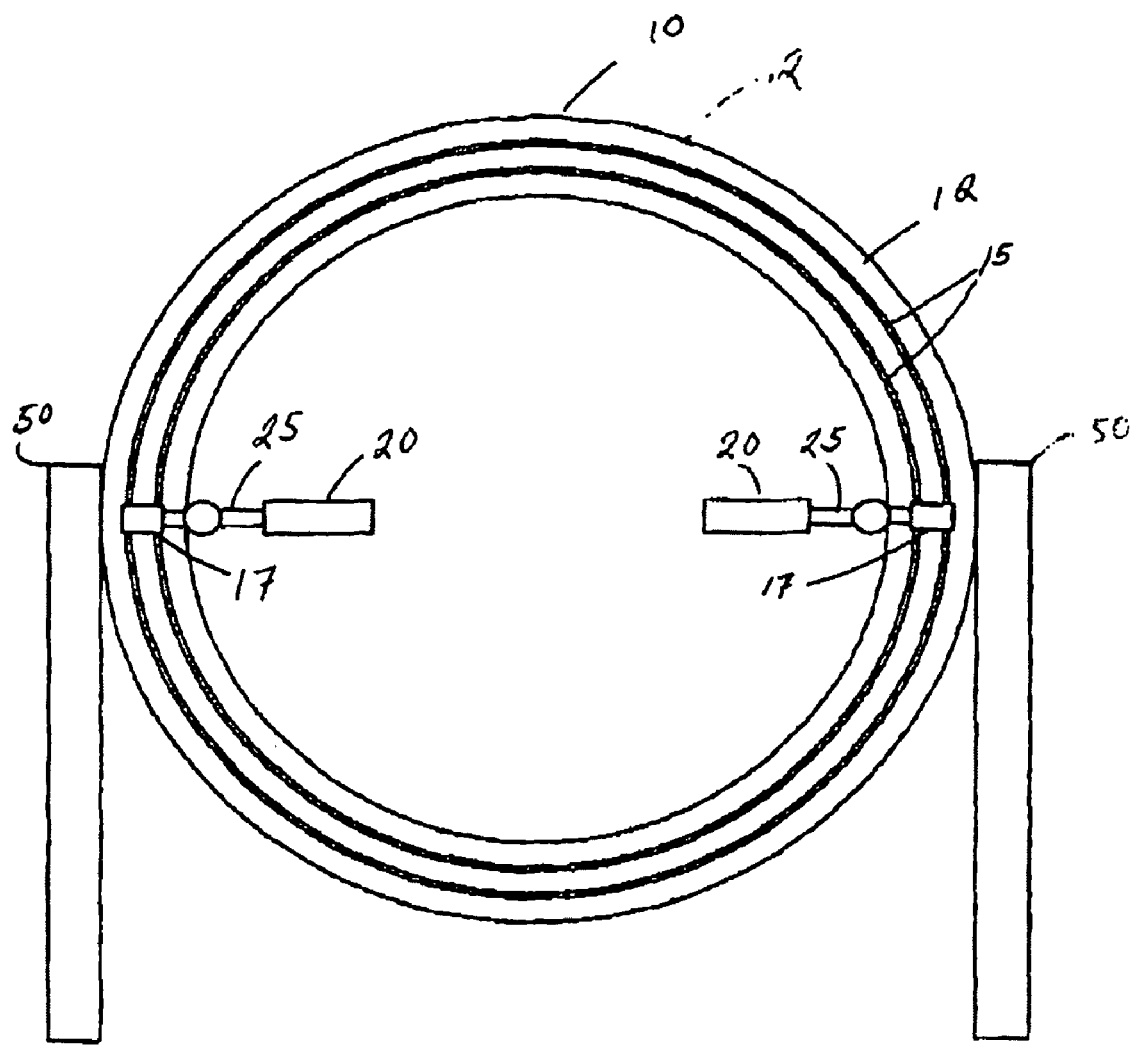
FIG. 4 is a schematic front elevational view of one embodiment of a microwave power assembly used in a system of the invention.

FIG. 4 is a side elevational view of microwave power assembly 10 depicted in FIG. 1.

Figure 5:
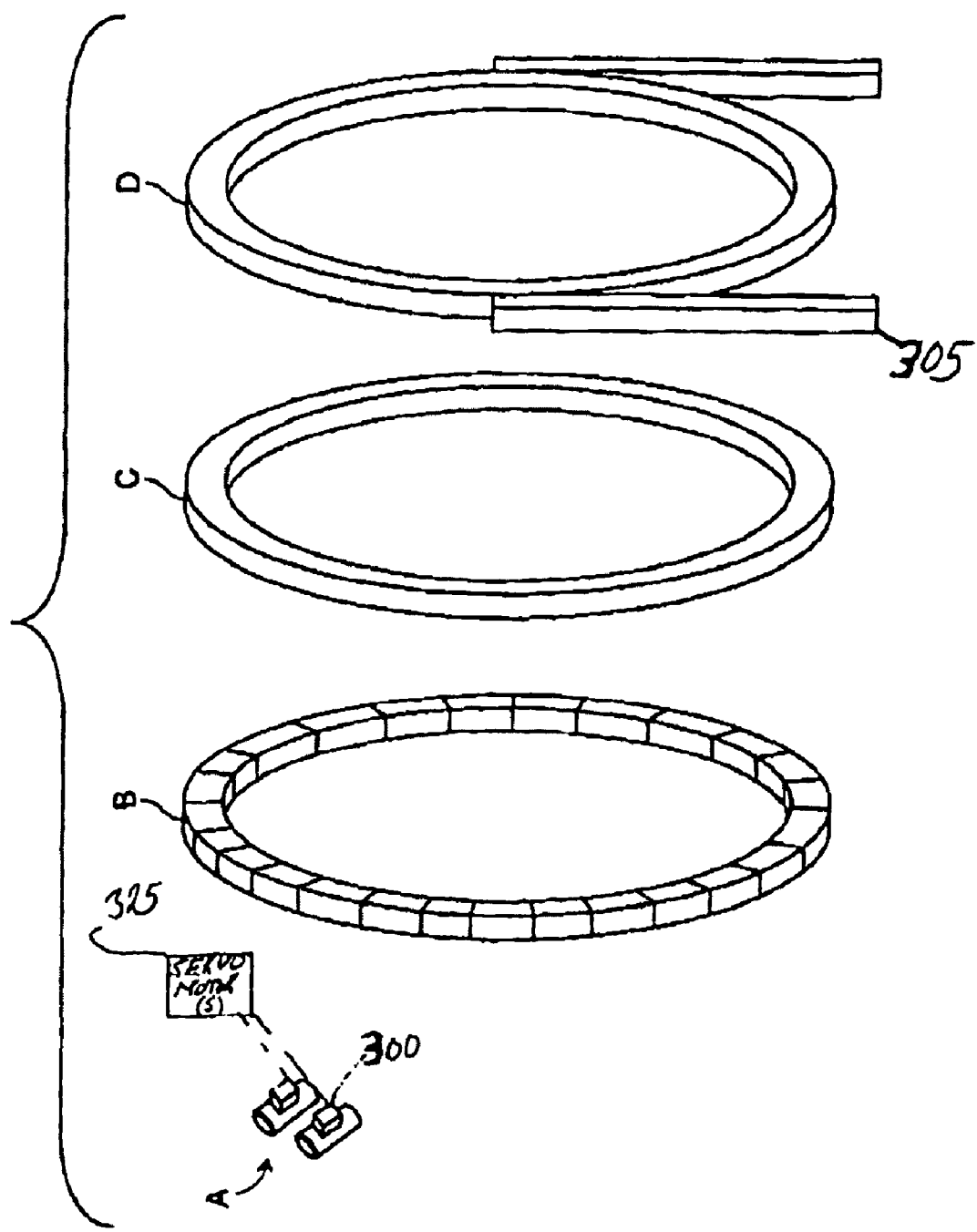
FIG. 5 is an exploded perspective view of one embodiment of a microwave power assembly used in a system of the invention.

FIG. 5 is an exploded perspective view of an embodiment of the microwave power assembly 10 depicted in FIGS. 1, 2, and 4. In FIG. 5, two microwave antennas A (corresponding to microwave power supply devices 20 in FIGS. 1, 2, and 4) are attachable to a track ring B by a robotic linkage 300 (corresponding to robotic arm 25 in FIGS. 1, 2, and 4). Antennas A each have servo motors 325 that allow them to be moved, independently of each other, circumferentially along track ring B. Servomotors 325 are connected to track B by couplings 17 (not shown). Track ring B is rigidly mounted to a circumferentially aligned support ring C. Support rings 15 in FIGS. 1, 2, and 4 are part of track ring B. Support ring C is mounted in a circumferentially movable manner relative to an annular support housing D, which corresponds to annular support frame or housing 12 in FIGS. 1-4. Annular support housing D is fixedly attached to two side upright support members 305, which correspond to supports 50 in FIGS. 1, 2, and 4. When support ring C rotates relative to annular support housing D, track ring B moves with support ring C and rotates microwave antennas A in tandem. Thus, microwave antennas A can move circumferentially independently of each other (via translation along track ring B under the action of servomotors 325) or in tandem (via rotation of support ring C relative to annular support housing D). In addition, robotic linkage 300 can further position antennas A, particularly radially (toward and away from the treated subject, and selectively at multiple angles to the subject).

Any plural number of microwave power supply devices (e.g., antennas A depicted in FIG. 5) can be used in systems of the invention. Positions of microwave power supply devices, wavelength control wave cancellation and reinforcement, and the optimization of such variables to affect targeting and range, can be controlled, e.g., as indicated in U.S. Pat. No. 5,922,013. The word "microwave" is nominally defined with reference to wavelengths from one to one hundred centimeters. Microwave power supply devices 20 (or A) typically used in the system of the invention include a transverse linear array of magnetron or other suitable components with appropriate local control circuitry.

On the basis of energy input requirements predetermined for given body weight, or sensing of energy absorption and body temperature, narrow incremental sections of the subject's body may be sequentially heated to a temperature adequate for a purpose such as killing infectious agents, such as bacteria or viruses, or undesired neoplasms such as tumors, in a continuous sequential process of one or more complete scans, thereby enabling cooling to take place promptly after desired heating is achieved, so as to eliminate permanent or temporary bodily injury. It will be appreciated, however, that in treatment of a fatal condition, some level of localized bodily damage or injury may be acceptable to the subject involved, in view of overall results which may be achievable.

In one embodiment, systems and methods of the invention use microwaves that are generated or delivered with a square waveform. A square waveform is generated by altering the dimensions and spacing of the cavities within a magnetron. Use of square waveform microwaves should enhance the treatment of infections and diseased cells. Use of square waveforms may improve therapeutic effect, reduce subject overheating, and minimize the need for patient cooling.

In other embodiments of the invention, a standard magnetron is used to generate microwaves, but the microwave waveform is modified. In still another embodiment of the invention, triangular waves and impulse "spikes" are used, either alone or in combination with square wave or sine waves.

Brain temperature during treatment must be maintained at safe levels. In this regard, the apparatus and methods described in U.S. Pat. No. 6,416,532, along with other appropriate techniques, can be used with systems and methods of the invention to ensure safe treatment. The complete disclosure of U.S. Pat. No. 6,416,532 is hereby incorporated by reference. The apparatus and methods described in U.S. Pat. No. 6,416,532 use direct impingement of a fine mist of coolant to effect a rapid and controlled cooling the brain of a patient. As illustrated in FIG. 1, sprayers 400 and 401 each generate a fine mist of coolant to achieve a rapid and controlled cooling the brain of a patient. This may be in accordance with the apparatus and methods described in U.S. Pat. No. 6,416,532. Such rapid and controlled cooling of the brain provides for maintaining the brain at a safe temperature, lower than 108° F. Rapid and controlled cooling of the brain can also be used to induce brain hypothermia, and unconsciousness, without medication. In a preferred embodiment, which departs from the teachings of U.S. Pat. No. 6,416,532, a fluid that exists in the gaseous state at or near room temperature, preferably liquid Nitrogen (but possibly also fluids such as carbon dioxide, alcohol, etc.), is used as a coolant and sprayed in a fine mist from sprayer 400, as shown in FIG. 7. In FIG. 7, cooling fluid is delivered from a storage device (not shown) through conduit 702 to sprayer tip 703, which emits a mist 711 of coolant fluid onto a target patch of skin 705 proximate the carotid artery on the neck 704 of patient 720. To prevent frostbite, protective skin cream (as for example used in Antarctic exploration) may be applied to the skin in the cooling area. The use of liquid Nitrogen avoids the need for collection apparatus as described in U.S. Pat. No. 6,416,532, because the liquid Nitrogen quickly evaporates. It also avoids the need for pumps, as the vapor pressure of the liquid Nitrogen is ample to drive sprayer 400 to generate the desired cooling mist.

In general, human cells start to die at around 110° F. Infectious cells and tumors can be killed at lower temperatures (e.g., cancer at 107° F. and tuberculosis at 108° F.). In treating disorders such as tuberculosis and lung tumors, it is therefore important to be able to monitor internal lung temperature, as in the embodiments of the invention described below.

Figure 6:
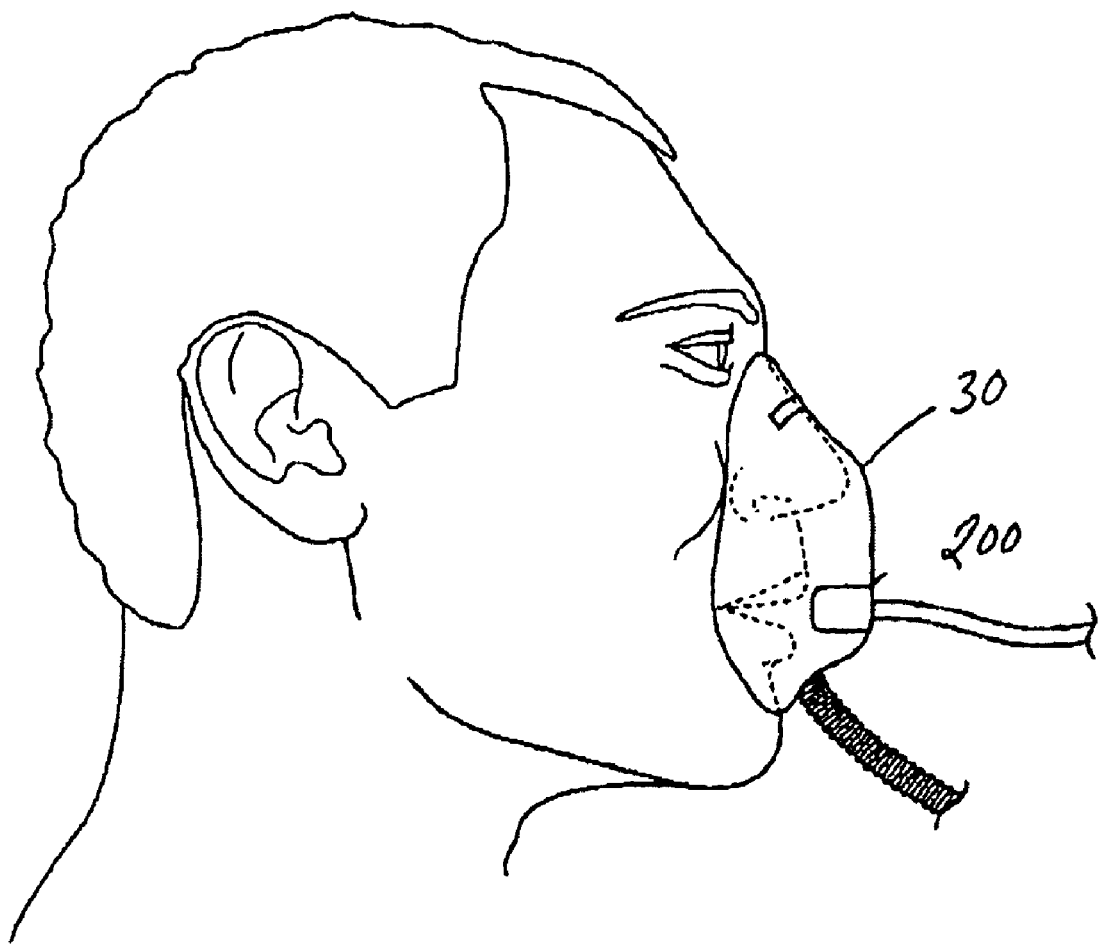
FIG. 6 is a schematic side elevational view of a device for detecting the temperature of air exhaled by the subject, which can be used in one embodiment of a system of the invention.
Figure 7:
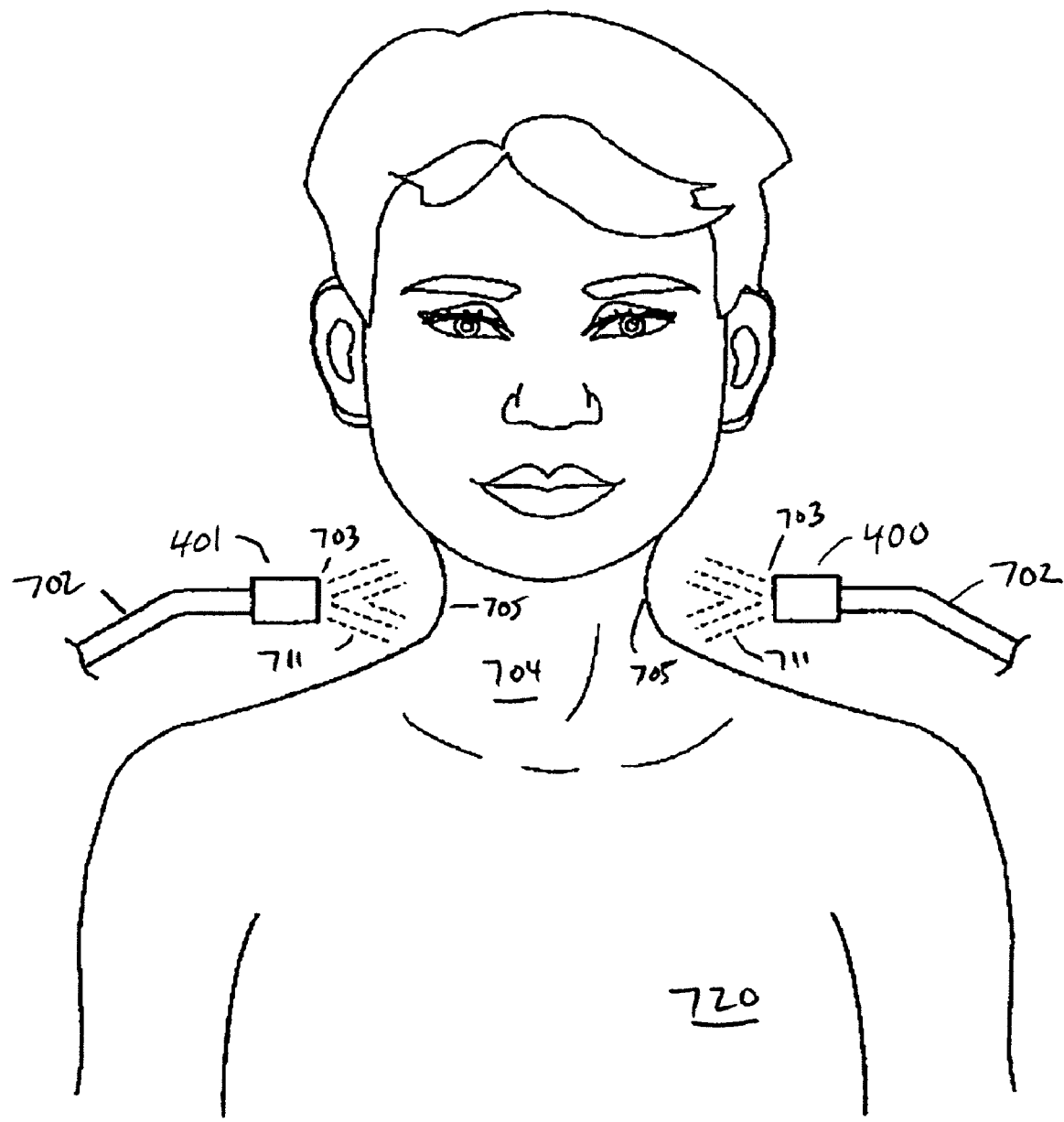
FIG. 7 is a schematic plan view of sprayers 400 and 401 as used to spray a fluid such as liquid Nitrogen that is in or near the gaseous state at room temperature.

As illustrated in FIG. 6, a thermocouple device 200 is positioned within a breathing port element (e.g., breathing mask) 30, where the subject exhales. The exhaled air temperature is measured by a thermocouple device 200 and is transmitted in electronic encoded form to central processing unit 40 (FIG. 1), which in turn extrapolates an internal lung temperature and adjusts the power level of the microwave power supply devices (not shown) accordingly. The temperature of the exhalant will be lower by some amount than the internal lung temperature, and the latter can be calculated within an acceptable range based on the former. In addition, normalized calibration may be performed prior to treatment by measuring the temperature of exhalant when the patient is breathing ambient air, and/or measuring the stabilized temperature of exhalant when the patient is given air to breathe at known elevated temperatures. Anesthesia could also be administered by breathing port element (e.g., breathing mask) 30 if necessary.

Optionally, temperature and other measurements are digitally recorded against a time base, so as to maintain a time line of relevant measurements.

Other inputs for calibration and/or normalization could include ambient (or supplied) air temperature and/or humidity, Barometric pressure, air flow velocity, and the size, weight and/or lung capacity of the patent.

Optionally, a nose clip could be used to force mouth breathing during the measurement and medical procedure.

The internal lung temperature can be approximated by the measured temperature of exhaled air. This could be a measurement by temperature sensor 120 at any time, but preferably would be a measurement when the subject is exhaling, as indicated by direction sensor 115 (or alternate means, such as a chest strap).

Generally, actual internal lung temperature will be higher than the temperature measured at sensor 120. At normal ambient temperatures (20-25° C.) the inhaled air will not in general heat up to the actual internal lung temperature. In addition, if the lungs are being heated, the exhaled air will have the opportunity to lose temperature on the way out of the breathing tract. Further cooling may take place in the measuring apparatus, as a result of surface conduction and mixing with non-exhaled air. The difference will be a function of at least the following: rate of breathing (slower tends toward higher exhalent temperatures); volume of breathing (deeper breathing tends toward higher exhalant temperatures); ambient temperature; humidity; barometric pressure; size; weight and/or lung capacity of the subject The invention is not limited to human use and may be used with animals.

The effect of the factors given above may be refined by further experimentation, if necessary.

It is evident that the embodiments described herein accomplish the stated objects of the invention. While the presently preferred embodiments have been described in detail, it will be apparent to those skilled in the art that the principles of the invention are realizable by other devices, systems and methods without departing from the scope and spirit of the invention, as defined in the following claims.

I claim:

1. A system to heat body portions using controlled microwave energy, comprising:
    (a) a support unit adapted to support a subject or subject body portion;
    (b) a microwave power assembly adapted for the receipt of the subject or subject body portion on said support unit, the microwave power assembly being further adapted to move translationally in an axial direction relative to the support unit and comprising two or more microwave power supply devices mounted to a support frame for mutually independent motion and, alternately, joint motion in tandem with one another, each of the two or more microwave power supply devices being capable of emitting a focused directional wave of microwave frequency energy at a controllable power level;
    (c) at least one position adjustment element arranged to electromechanically position the microwave power assembly and the two or more microwave power supply devices relative to the subject or subject body portion on said support unit; and
    (d) a central processor unit that is in electronic communication with the position adjustment element and the two or more microwave power supply devices, that is adapted to control the positioning of the microwave power assembly and the two or more microwave power supply devices, and that is arranged to control at least one of the power level, the wave focus, the wavelength, phase, wave direction, and waveform of each of the waves of microwave frequency energy emitted by the microwave power supply devices,
    wherein the microwave power assembly further comprises:
        (i) an annular support housing;
        (ii) a support ring positioned within, and adapted for circumferential movement relative to, the annular support housing;
        (iii) a track ring positioned within, and affixed to, the support ring; and
        (iv) two or more microwave antennas that are affixed to the track ring and that are adapted to move (A) circumferentially and independently of each other by translation along the track ring, or (B) in tandem by rotation of the support ring relative to the annular support housing.

2. The system of claim 1, wherein the annular support housing is supported on each side by upright members that are adapted for translational movement along tracks that are positioned beneath, and in an axial direction relative to, the annular support housing.

3. The system of claim 1, wherein the two or more microwave antennas are each coupled to servo motors that are adapted to move each of the two or more microwave antennas, independently or in tandem, radially or circumferentially, along the track ring.

4. A system to heat body portions using controlled microwave energy, comprising:
    (a) a support unit adapted to support a subject or subject body portion;
    (b) a microwave power assembly adapted for the receipt of the subject or subject body portion on said support unit, the microwave power assembly being further adapted to move translationally in an axial direction relative to the support unit and comprising two or more microwave power supply devices mounted to a support frame for mutually independent motion and, alternately, joint motion in tandem with one another, each of the two or more microwave power supply devices being capable of emitting a focused directional wave of microwave frequency energy at a controllable power level;
    (c) at least one position adjustment element arranged to electromechanically position the microwave power assembly and the two or more microwave power supply devices relative to the subject or subject body portion on said support unit; and
    (d) a central processor unit that is in electronic communication with the position adjustment element and the two or more microwave power supply devices, that is adapted to control the positioning of the microwave power assembly and the two or more microwave power supply devices, and that is arranged to control at least one of the power level, the wave focus, the wavelength, phase, wave direction, and waveform of each of the waves of microwave frequency energy emitted by the microwave power supply devices,
    wherein said support frame defines an at least partially circular track, said two or more microwave power supply devices being mounted to said support frame for alternately independent and joint motion circumferentially along said track and alternately independent and joint motion radially relative to said track.

5. The system of claim 4, wherein the microwave power assembly further comprises:
(i) an annular support frame or housing; and
(ii) a track ring mounted at least indirectly to the annular support frame or housing for circumferential movement relative to the annular support frame or housing,
(iii) said two or more microwave power supply devices being attached to the track ring for movement (A) circumferentially and independently of each other by translation along the track ring, or (B) in tandem by rotation of the track ring relative to the annular support frame or housing.

6. The system of claim 4 wherein said microwave power assembly is movable translationally along an axis of said support unit.

\* \* \* \* \*